United States Patent [19]

Beck et al.

[11] Patent Number: 4,877,030
[45] Date of Patent: Oct. 31, 1989

[54] DEVICE FOR THE WIDENING OF BLOOD VESSELS

[76] Inventors: Andreas Beck, W. Hausensteinstrasse 10a, 7746 Hornberg; Norbert Nanko, 7800 Freiburg, both of Fed. Rep. of Germany

[21] Appl. No.: 200,380

[22] Filed: May 31, 1988

[30] Foreign Application Priority Data

Feb. 2, 1988 [DE] Fed. Rep. of Germany ....... 3803003

[51] Int. Cl.⁴ ............................................. A61M 29/02
[52] U.S. Cl. .................................... 128/343; 128/341; 128/344; 128/303.11; 623/1
[58] Field of Search ........... 128/341, 343, 344, 303.11, 128/334 R; 623/1, 12, 66

[56] References Cited

U.S. PATENT DOCUMENTS

| | | | |
|---|---|---|---|
| 2,085,368 | 6/1937 | Kendall | 128/341 |
| 4,593,692 | 6/1986 | Flowers | 128/344 X |
| 4,617,932 | 10/1986 | Kornberg | 623/1 X |
| 4,650,466 | 3/1987 | Luther | 128/343 X |
| 4,740,207 | 4/1988 | Kreamer | 128/343 X |

*Primary Examiner*—Alan W. Cannon
*Attorney, Agent, or Firm*—Jones, Askew & Lunsford

[57] ABSTRACT

Device for the widening of blood vessels having a catheter (5) in whose front end area an elongate, inflatable balloon (6) is present, with the outside of the uninflated balloon (6) being wound round with a woven material (1) of such a length that its end edges (2), provided with a border, overlap. After introduction into the vessel and widening, the woven material serves as a vessel prosthesis.

7 Claims, 2 Drawing Sheets

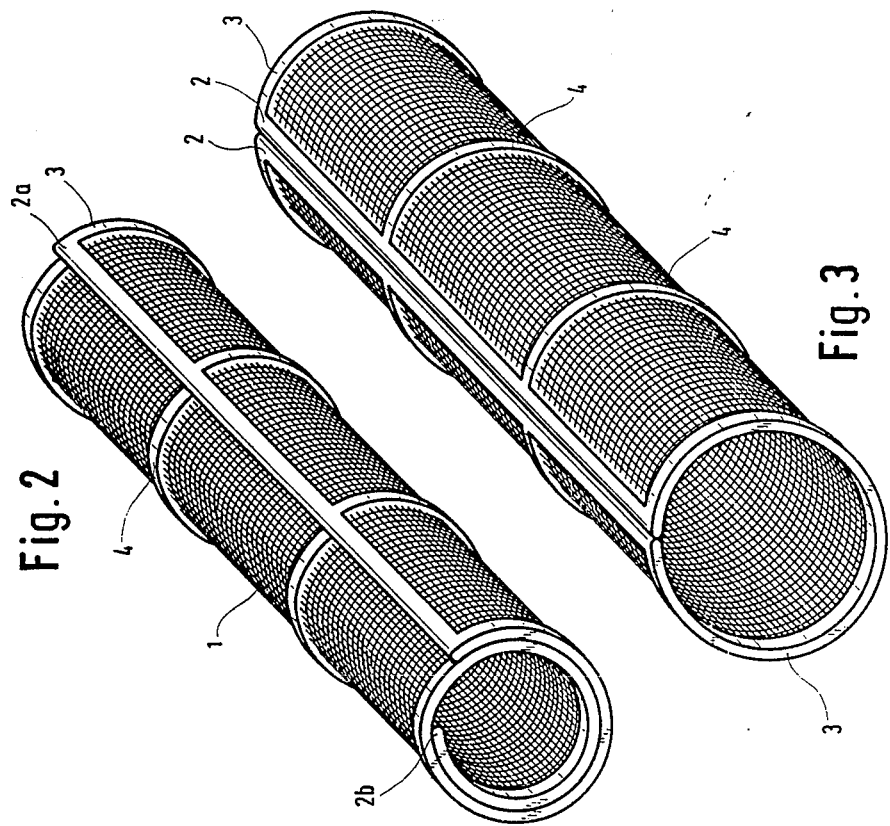
Fig. 2
Fig. 3
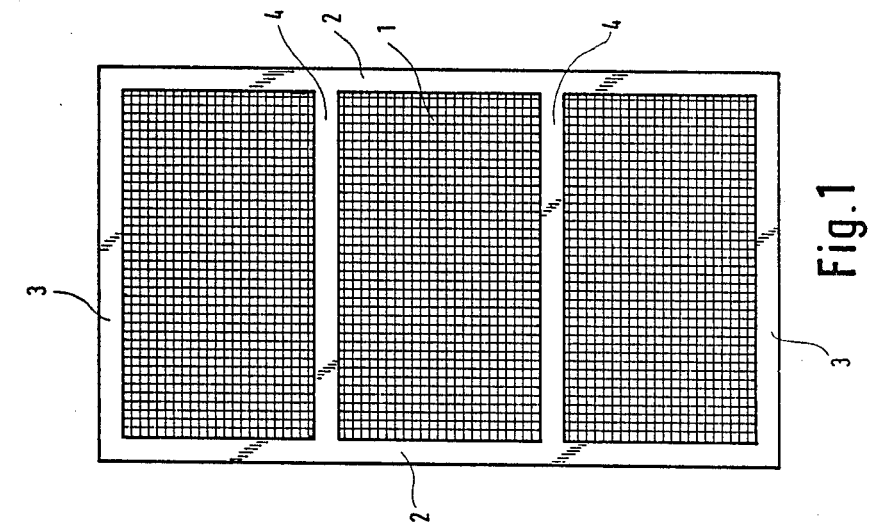
Fig. 1

DEVICE FOR THE WIDENING OF BLOOD VESSELS

The invention relates to a device for the widening of blood vessels.

Dilation catheters with an inflatable balloon, called balloon catheters, which are inserted into blood vessels with the balloon uninflated and the balloon then widened at the desired position, are known in principle in a wide variety of embodiments. Resilient metallic meshes have also previously been used for dilating, being inserted into the vessel in compressed form and enlarged to the desired diameter after removal of the insertion catheter (cf. Martine Mazieres in Panorama du Medecin - No. 2517, April 1987).

However, these endoprostheses for vessels are not satisfactory to a sufficient extent.

The object of the present invention is to provide an improved device for the widening of blood vessels which, in the event of stenoses or occlusions, once more guarantees the bloodflow so that the downstream extremity or the succeeding organ remains supplied with circulating oxygen and thus remains healthy.

This object is achieved by a device for the widening of blood vessels with a catheter in whose front end area an elongate, inflatable balloon is present, and wherein the outside of the uninflated balloon is wound round with a woven material of such a length that its end edges, provided with a border, overlap.

The end edges and the woven material overlap so far around the outer surface of the uninflated balloon that, after inflating the balloon, the end edges abut flush and even. That is, the extent of the overlapping depends on the desired final diameter of the endoprosthesis and can amount to a multiple of the outer periphery of the uninflated balloon.

The woven material preferably also has borders at the side edges. In the case of synthetic woven materials, the borders are also of synthetic material. However, they may contain a metal wire for reinforcement. In order to stabilize the shape of the endoprosthesis, reinforcements may be present running, at a distance from and parallel to the bordered side edges, from end edge to end edge. In the case of synthetic woven materials, the reinforcements may be of synthetic material or of metal or of metal wires encased in synthetic material whose ends are anchored in the borders of the end edges. When using metal wires as reinforcements, the first reinforcements are preferably arranged directly alongside, ie. at a short distance from, the bordered side edges. The combination of synthetic woven material with metallic reinforcements and metallic insets in the borders has the advantage that the metal fibers or wires act as X-ray contrast agent and facilitate visualization of the position of the endoprosthesis.

In the case of metallic woven materials, the borders and reinforcements are also of metal. The number of reinforcements depends on the length in the widened state of the cylindrical woven material bodies. The preferred distance of reinforcements from each other is 10 to 20 mm, preferably, depending on the length of the prosthesis, in each case after ⅓ of the length, e.g. with a length of woven material of 3 cm, two reinforcements after 1 cm in each case.

The woven material arranged on the balloon is preferably a fabric or mesh with from 20 to 150 filaments per cm and filament diameters of 0.032 mm to 0.15 mm. Very particularly preferred filament diameters are 0.1 mm to 0.15 mm and fabric with filament numbers of 25 to 50 filaments per cm. The fabric is preferably arranged on the balloon so that the filaments of the fabric run parallel to the end edges and the side edges. If, on the other hand, the mesh is arranged such that the filaments run oblique to the end edges, then, in the case of non-bordered side edges and no reinforcements and no firm connections at the cross-over points of the filaments, it is possible for the distance of the bordered end edges of the woven material from each other to be reduced by compression, and thus the overlapping of the end edges required when winding around the balloon is made shorter. When widening, the angle of the filaments of the gauze relative to each other changes and at the same time leads to a reduction in the length of the hollow cylindrical woven material. In order to avoid this, it is preferred also to provide the side edges of the woven material with borders and to provide reinforcements running from end edge to end edge, so as to avoid a compression of the woven material and a change in the position of the filaments of the gauze relative to each other.

Most medically tolerated plastics, such as medically tolerated polyvinyl chloride, polyethylene, polyamide, polyester and polycarbonates, have proven to be suitable plastic woven materials.

The particularly preferred metals for woven materials or reinforcements are noble metals and/or base metals with noble-metal coating.

In order to stabilize the meshes of the woven material, thermal treatments and pressing can be carried out on plastic woven materials.

In the case of metallic woven materials, a pressing is preferably carried out before the winding onto the uninflated balloon of a balloon catheter, in order to achieve as level a woven material structure as possible.

The rectangular woven material sections or parts are wound onto the outside of a balloon of so-called balloon catheters. Coaxial catheters of this type are known. Rubbers reinforced with nylon fiber materials have proven to be suitable balloon material. In order to reduce the friction at the face of the balloon catheters, the surfaces are coated with polyurethane. Such balloons resist a pressure of up to 12 atm. In the inflated state, the elongate balloons can have outer diameters of 4 to 10, preferably 5 to 8 mm. The balloon length is between 20 and 50 mm. Preferred balloon lengths are 25 to 40 mm. This permits the winding of woven materials of corresponding length onto the uninflated balloon with varying lengths.

The use of fabric in the preferred arrangement of the filaments, in which the filaments run parallel or perpendicular to the borders, and of the fixing of the outer periphery of the woven material by bordering the side edges and applying reinforcements, has the advantage that the length of the endoprosthesis does not change on expansion of the vessel stent located in a blood vessel. The desired size can thus already be set before use. The high dilation pressure which is possible with the preferred balloon catheters means that the vessel is opened optimally on use of the device according to the invention, and redilatation is in many cases avoided.

The device according to the invention serves for the widening of blood vessels, in which connection the widened woven material body remains in the blood vessel as a so-called vessel stent or endoprosthesis.

The procedure for the use according to the invention of the device is as follows:

The woven materials which are wound around a commercially available Olbert balloon catheter from Maedox Surgimed A.S. with catheter diameters of 1.5 mm to 2.1 mm and balloon diameters in the non-widened state of 2.0 to 2.6 mm, and which, in the widened state, are intended to serve as endoprostheses for blood vessels, are guided along with the balloon catheter, using the transfemoral technique, via an access of about 2.7 mm as far as the stenosis to be widened and then widened in the stenosis by expanding the balloon. The stenoses are first passed through by the guide wire of the catheter, and then the balloon and the woven material arranged thereon are introduced into the stenosis itself. Then, with radiological monitoring, the balloon of the catheter is charged with X-ray contrast fluid at a pressure of up to 10.13 bar and is dilated to the desired final diameter. After removal of the hydrostatic pressure, the balloon catheter is removed again, and the widened woven material remains as endoprosthesis in the blood vessel. The endoprostheses are preferably used in the femoral artery and in blood vessels in the pelvic region and in the artery of the knee, in the renal artery and in vessels in the neck/head area.

The invention will now be illustrated in greater detail with reference to the figures.

FIG. 1 shows a rectangular piece of woven material in the unrolled state.

FIG. 2 shows the same woven material in rolled form, but without the balloon catheter for support.

FIG. 3 shows the woven material widened into a hollow cylinder with abutting end edges.

FIGS. 4 and 4a show the balloon catheter in the non-dilated and dilated states, but without the woven material wound on.

Figure 4A:
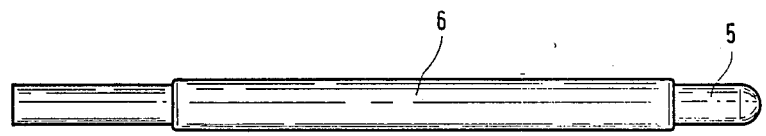

The rectangular piece of woven material (1) shown in FIG. 1 has bordered end edges (2) and bordered side edges (3), and reinforcements (4) running parallel to the side edges. In this case the woven material is cut out from a larger piece of woven material such that the filaments of the gauze run parallel and perpendicular to the bordered edges.

FIG. 2 shows the woven material (1) in the form in which it is wound onto the unexpanded balloon catheter (not shown). The woven material is rolled up so far that the end edges (2) and (2b) overlap considerably. The bordered side edges are designated (3) and the reinforcements are designated (4). Increasing the diameter of the cylindrically wound-on metallic woven material (1) results in the design, shown in FIG. 3, of the cylindrical woven material or woven material body, acting as an endoprosthesis, with abutting end edges (2). In analogy to the previous figures, the side edges are designated (3) and the reinforcements are designated (4).

Figure 4B:
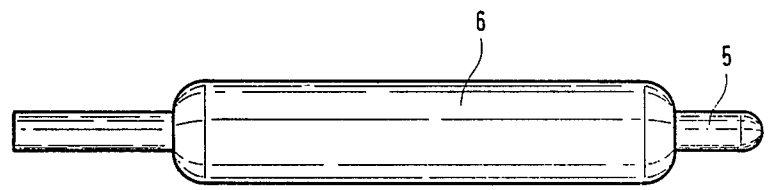

FIG. 4a shows a balloon catheter (5) with a balloon (6) in the uninflated state arranged on the outer surface. FIG. 4b shows the balloon (6) in the inflated state on the catheter (5).

Figure 5:
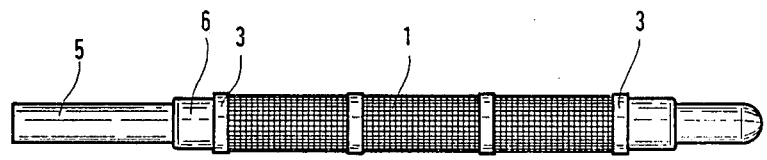
FIG. 5 shows the device according to the invention with the as yet uninflated balloon, and the woven material on its surface.

FIG. 5 shows the device according to the invention with a balloon catheter (5), with a balloon (6), on whose outer surface the woven material (1) is wound. The bordered side edges of the woven material (1) are designated (3).

Figure 6:
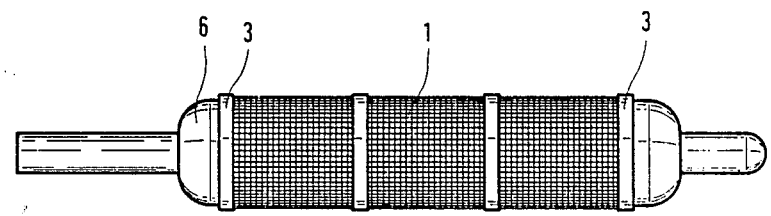
FIG. 6 shows the device according to the invention with the balloon inflated and the correspondingly expanded woven material on its surface.

FIG. 6 shows the inflated balloon (6) and the woven material (1) widened to the final size. The abutting reinforced edges of the woven material stabilize the cylindrical shape of the woven material serving as endoprosthesis.

EXAMPLE 1

A piece 2.5 cm×7 cm in size is cut out from a mesh of gold-plated brass wire with a diameter of 0.032 mm and with 124 filaments per cm in such a way that the filaments run parallel and perpendicular to the edges and the woven material is bordered at the edges with gold solder. At a distance of in each case about 2 cm from the narrow edges of the rectangular piece of woven material, in each case two wires running parallel between the longitudinal edges are filled in with gold solder by filling in the intermediate meshes, in order to strengthen the woven material. The woven material is wound onto the balloon of a balloon catheter in the way shown in FIGS. 2 and 5 so that the outer diameter is 4 mm.

EXAMPLE 2

A piece 0.5 cm×2 cm in size is cut out from a fabric of platinum wire with a wire diameter of 0.063 mm with 56 filaments per cm in such a way that the filaments run parallel and perpendicular to the edges and the woven material is bordered at the edges with platinum solder. In the middle, between the narrow edges of the rectangular piece of woven material, in each case the meshes between two wires running parallel to the longitudinal edges are filled in with platinum solder as reinforcement. The woven material is wound onto the balloon of a commercially available balloon catheter in the way shown in FIGS. 2 and 5 so that the outer diameter is about 2 mm.

EXAMPLE 3

A piece 1.0 cm×4 cm in size is cut out from a gauze of gold-plated brass wire with a wire diameter of 0.125 mm and a filament number of 125 filaments per cm in such a way that the filaments run parallel and perpendicular to the edges. The edges are bordered with gold solder and, for reinforcement, meshes between two wires running parallel between the longitudinal edges are filled in with solder. The woven material thus prepared is wound onto the balloon of a balloon catheter in the way shown in FIGS. 2 and 5, with the longitudinal edges, provided with a border, overlapping and the outer diameter being about 3.5 mm.

EXAMPLE 4

A fabric of polyester filaments with a filament diameter of 0.15 mm and 23 filaments per cm is cut to a size of 2 cm×5 cm so that the filaments run parallel and perpendicular to the edges. One gold-plated brass wire running between the edges and having a diameter of 0.15 mm is in each case drawn into the last mesh before the edges, and the edges of the woven material are reinforced by heating the thermoplastic material to a temperature at which the cross-over points of the filaments bond firmly to each other. Any protruding filament ends are removed so that in each case a filament running in the direction of the edge forms the edge. For reinforcement between the longitudinal sides, gold-plated brass wires were also, before heating, introduced, into the woven material at a distance of 1 cm from the narrow sides and from each other. The woven material thus strengthened is wound onto the balloon of a balloon catheter so that the bordered longitudinal edges overlap, as shown in FIGS. 2 and 5.

EXAMPLE 5

A piece of mesh 3 cm×7 cm in size is cut from a nylon woven material with monofilaments of a diameter of 0.105 mm and a filament number of about 40 filaments per cm, and the edges are reinforced and bordered as indicated in Example 4. In the same way, reinforcement wires are also drawn in between the longitudinal edges, and the ends of the gold-plated wire are integrated into the edge border and reinforcement. In order to eliminate projections, the edges are pressed together between heated metal frames. The woven material thus finished is wound onto the balloon of a balloon catheter for insertion to be used as a vessel prosthesis.

We claim:

1. A device having a non-widened state for insertion within a blood vessel and selectively expandable therewithin by means of a balloon catheter or the like, the device comprising:

a generally rectangular panel of a relatively flexible woven material and having end edges and side edges;

the panel being wound around in a generally cylindrical shape with the end edges overlapping each other in the non-widened state, and with internal area sufficient to accommodate a balloon catheter or the like;

reinforcing means defining an end border and reinforcing each end edge of the woven material, each such reinforcing end border having a surface coplanar with the panel and parallel to the corresponding end edge of the panel;

reinforcing means defining a side border along and reinforcing each side edge of the panel; and the end borders being operative to move into manual abutment when the panel is unwound by inflation of a balloon catheter or the like to unwind and widen the cylindrical shape to an extent that the end edges no longer overlap, so that the surfaces of the end borders abut one another and maintain the widened cylindrical shape of the device within a blood vessel.

2. A device as in claim 1 wherein the woven material is a fabric which is arranged on the balloon catheter or the like so that the filaments of the fabric run parallel to the end edges and side edges of the panel.

3. A device as claimed in claim 1 wherein the woven material has reinforcements running, at a distance from and parallel to the bordered side edges, from end edge to end edge.

4. A device as claimed in claim 1, wherein the woven material is a fabric with 20 to 150 fibers per cm and fiber thickness of 0.03 mm to 0.15 mm.

5. A device as claimed in claim 1, wherein the woven material is of synthetic material.

6. A device as claimed in claim 1, wherein the woven material is of metal.

7. A device as claimed in claim 6, wherein the metal fibers of the woven material are of noble metal and/or of metal with noble-metal coating.

* * * * *